United States Patent [19]

Griffith

[11] Patent Number: 5,047,541
[45] Date of Patent: Sep. 10, 1991

[54] 2-AZACYCLOCARBOXAMIDE DERIVATIVES

[75] Inventor: Ronald C. Griffith, Pittsford, N.Y.

[73] Assignee: Fisons Corporation, Rochester, N.Y.

[21] Appl. No.: 366,070

[22] Filed: Jun. 14, 1989

Related U.S. Application Data

[63] Continuation-in-part of Ser. No. 11,981, Feb. 6, 1987, abandoned.

[51] Int. Cl.$^5$ .............................................. C07D 211/32
[52] U.S. Cl. ................................... 546/225; 548/200; 548/537
[58] Field of Search ............... 546/225; 548/200, 537; 514/330

[56] References Cited

U.S. PATENT DOCUMENTS

| 3,489,753 | 1/1970 | Ostermayer et al. | 514/906 |
| 3,655,680 | 4/1972 | Allen et al. | 514/906 |
| 3,692,784 | 9/1972 | Lindberg et al. | 548/577 |

FOREIGN PATENT DOCUMENTS

| 776188 | of 1971 | Belgium . |
| 955508 | of 1957 | Fed. Rep. of Germany . |
| 343388 | of 1960 | Switzerland . |
| 416626 | of 1967 | Switzerland . |
| WO85/00599 | of 1985 | World Int. Prop. O. . |

OTHER PUBLICATIONS

CA 73,25044n, Abstracting Bol. Soc. Quim Peru 35(3), 77–84 (1969).
CA 85,5705y, Abstracting Japan Kokai 50/130776 (1975).
CA 96,19744z, Abstracting Prakt. Akad. Athenon 54(A–B) 383–397 (1980).
CA 79,66777w, Abstracting Murano et al., Agr. Biol. Chem. 37(5), 981–988 (1973).
English translation of German patent 955,508.
J. Ritchie, et al., in "Goodman and Gilman's The Pharmacological Basis of Therapeutics," 7th ed., Ch. 15, 302–321, MacMillan, N.Y. (1985).

Primary Examiner—Glennon H. Hollrah
Assistant Examiner—Mark W. Russell
Attorney, Agent, or Firm—Seidel, Gonda, Lavorgna & Monaco

[57] ABSTRACT

Compounds are provided of the following general structure:

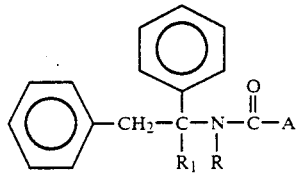

wherein A is 2-pyrrolidinyl, 2-piperidinyl or 4-thiazolidinyl and R and $R_1$ are independently selected from hydrogen and methyl. They are useful for providing sedative and antiepileptic activity.

2 Claims, No Drawings

2-AZACYCLOCARBOXAMIDE DERIVATIVES

CROSS REFERENCE TO RELATED APPLICATION

This is a continuation-in-part of co-pending application Ser. No. 011,981, now abandoned filed Feb. 6, 1987.

SUMMARY OF THE INVENTION

Novel substituted 2-azacyclocarboxamide derivatives have been prepared and found to possess useful sedative and neuroprotective properties, especially antiepileptic activity.

GENERAL DESCRIPTION

This invention relates to novel 2-azacyclocarboxamide compounds of the following general structure (1):

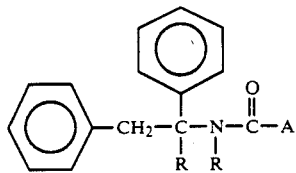

(1)

wherein A is 2-pyrrolidinyl, 2-piperidinyl or 4-thiazolidinyl and R and $R_1$ are independently selected from hydrogen or methyl.

This invention also relates to diastereomeric and optically resolved forms and mixtures thereof, and to pharmaceutically acceptable acid addition salts of the compounds of general formula (1).

Compounds of this invention possess useful pharmaceutical properties. In particular they posses sedative and neuroprotective properties, especially antiepileptic activity.

DETAILED DESCRIPTION

The 2-azacyclocarboxamides of general formula (I) as described fully above are conveniently prepared by suitable amide bond forming reactions from the corresponding amine intermediates of general formula (2):

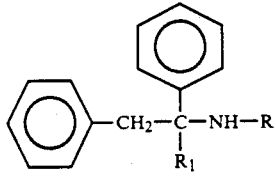

(2)

where $R_1$ and R are as defined above.

Most of the amines of the general formula (2) are known compounds and may be purchased commercially or conveniently prepared by suitable modifications of the reported procedures. Amines of the general formula (2) which are not known are prepared by similar procedures. The preparation of amines of general formula (2) is described in the "Preparation of Intermediates" section.

The preferred method of amide bond formation consists of direct coupling of an amine of general formula (2) with a suitably N-protected cyclic amino acid, where the nitrogen is protected as a urethane, preferably as a benzyloxycarbonyl (CBZ) or a t-butyloxycarbonyl (BOC) urethane, in an inert solvent in the presence of a coupling reagent such as dicyclohexylcarbodiimide with or without 1-hydroxybenzotriazole or other additives to provide N-protected coupled products. The protecting groups are then readily removed by either catalytic hydrogenation for the CBZ group or treatment with an acid such as trifluoroacetic or hydrochloric acid for the BOC group to provide compounds of the general formula (1).

The compounds of general formula (1) possess asymmetric centers, and therefore geometric and optical isomers are possible. Such compounds may be conveniently prepared from optically active amines of formula (2) and/or from optically active amino acid intermediates by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The compounds of general formula (1) possess useful pharmaceutical properties. In particular they possess useful sedative and neuroprotective properties. Most particularly, the compounds are useful as N-methyl-D-aspartate (NMDA) receptor blockers.

Excessive excitation of central neurons by neurotransmitters can cause degeneration of the neurons, which may result in disorders such as stroke, cerebral ischaemia, epilepsy, aging and Alzheimer's disease. Agonists acting at NMDA receptors cause excitatory neurotransmission, and compounds with NMDA blocking properties may be useful as neuroprotectives for the treatment of the aforementioned pathological conditions. Compounds with anticonvulsant properties may be particularly useful in the treatment of epilepsy. Compounds with antihypoxic properties may be particularly useful in the treatment of stroke. All of these activities may be measured by standard assays.

NMDA Blockinq Assays

NMDA blocking activity is measured by assessing a compound's ability to protect mice from convulsions induced by intravenous administration of 150 m/k of NMDA according to the procedures of Czuczwar et al., (*Neurotransmitters, Seizures and Epilepsy III*, edited by G. Nistico et al., Raven Press, New York 1986, pages 235-246). Groups of mice are pretreated for 30 minutes with test compound by oral or intraperitoneal routes. They are thereafter given NMDA. Animals are observed for convulsions as defined by loss of righting reflex. Animals are kept for 60 minutes after NMDA dosing. Mortality is recorded.

NMDA blocking activity is also measured electrophysiologically in vitro by measuring NMDA receptor activity in rat hippocampus tissue slices. Two assays are used.

According to a first electrophysiological assay, application of 20 μM NMDA to tissue slices of rat hippocampus (450 μm thick) for approximately 2 minutes causes a massive depolarization of hippocampal neurons, and a profound reduction of the synaptic field potential. To examine potential NMDA antagonism a base line effect is determined by repeated applications of NMDA and measurement of the resulting reduction of the synaptic response. The test compound is then included in the buffer bathing the slice, and then NMDA is reapplied. NMDA antagonists will block the reduction in field potential produced by NMDA. The effect of drug-treated slices is compared to untreated slices.

The protocol for the aforesaid assay is as follows:

A. Slices of rat hippocampus (450 μm thick) are prepared from young adult male Sprague-Dawley rats using published procedures and a conventional physiological buffer.

B. A NaCl-filled glass microelectrode is used to record extracellular synaptic field potentials from hippocampal area CAI following electrical stimulation of the Schaffer collateral input. Stimulus intensity (0.02 msec duration, amplitude 5-15V) is adjusted to yield a 2-3 mV synaptic field potential; one stimulus is given every 20 seconds. The amplitude of each field potential at a fixed interval after stimulation is measured and displayed on a polygraph using a sample-and-hold amplifier.

C. Application of 20 μM NMDA for approximately 2 minutes causes a massive depolarization of hippocampal neurons, and a profound reduction of the synaptic field potential (analogous to depolarization block); the synaptic field potential recovers within 5-10 minutes of washing out NMDA. Thus, the NMDA "response" in this test is a reduction of the synaptic response The NMDA effect is expressed as a percentage reduction of baseline response amplitude (e.g., 50% indicates that the response was reduced by half).

D. NMDA can be applied repeatedly, but several minutes must be allowed for the slice to recover from the challenge. To examine potential NMDA antagonism in this test, several NMDA applications are made to determine a baseline effect. The compound is then included in the buffer bathing the slice, and NMDA is re-applied 3-4 times. The drug is then washed out, and NMDA is applied 2-4 more times. NMDA antagonists will block the effect of NMDA (i.e., prevent the response reduction produced by NMDA). The effect of the drug-treated slices are compared to untreated slices (NMDA only, no test compounds).

According to a second electrophysiological assay for NMDA blocking activity, rat hippocampal slices (450 μm thick) are pretreated with a buffer containing 10 μM 6,7-dinitroquinoxaline-2,3-dione (DNQX) and magnesium (25 μM). Under these conditions the synaptic response is almost entirely mediated by NMDA receptors. To evaluate NMDA antagonism, test compounds are added to the buffer and the synaptic field potentials are compared before and during treatment. The decrease in response caused by the drug is expressed as a percentage of the pre-drug response.

The protocol for the aforesaid assay is as follows:

A. Hippocampal slices (450 μm thick) are prepared from young adult male Sprague-Dawley rats using published procedures. The buffer used contains 10 μM DNQX, a potent competitive antagonist of quisqualate/kainate receptors. In addition, the buffer contains a relatively low concentration of magnesium (25 μM) to enhance responses mediated via NMDA receptors (magnesium blocks the NMDA-activated channel). Thus, under these conditions, the synaptic response is almost entirely mediated by NMDA receptors.

B. Synaptic field potentials are recorded extracellularly in hippocampal area CA1 following electrical stimulation of the Schaffer collateral input to CA1. The recording electrode consists of a fine glass micropipette filled with 1M NaCl, and the stimulating electrode consists of a twisted pair of Teflon ®-insulated stainless steel 100 μm wires. The stimulus intensity (duration 0.01-0.03 msec, amplitude 5-15V) is adjusted to elicit a 1.5-3mV synaptic field potential. One stimulus is delivered every 20 seconds. The peak amplitude of each synaptic response is measured and plotted online using a microprocessor.

C. To evaluate potential NMDA antagonism, test compounds are added to the buffer for up to 30 minutes, and the synaptic field potential amplitude is compared before and during treatment. The response decrease caused by the drug is expressed as a percentage of pre-drug response (or of an extrapolated baseline if response amplitude is slowly changing before drug application). If no drug effect is seen, the standard NMDA competitive antagonist 2-amino-5-phosphonopentanoic acid (AP5) is applied (10 μM) to verify that the system is operating properly. At 10 μM, AP5 has been found consistently to produce a 70% decrease in the synaptic response under these conditions.

D. Drug-treated slices are compared to buffer-treated control slices to determine statistical significance (ANOVA followed by Newman-Keuls analysis).

Antiepileptic Assay

Antiepileptic activity was measured by assessing a compound's ability to prevent the hind limb tonic extension component of the seizure in groups of mice induced by maximal electroshock after oral or intraperitoneal administration according to the procedures of the Epilepsy Branch, NINCDS as published by R. J. Porter, et al., *Cleve. Clin. Quarterly* 1984, 51. 293, and compared to the standard agents dilantin and phenobarbital. Activities in the range of 10-400 m/k after oral administration in this assay system were obtained Sedative activity was assessed by behavioral observation in groups of mice by standard literature procedures. Selected compounds exhibited activity in the range of 30-600 m/k in this assay.

Antihypoxia Assay

The compounds of this invention also possess useful antihypoxia activity, that is, they extend the lifetime of animals exposed to a hypoxic environment. This activity is conveniently measured in mice. Groups of mice are tested at various times after the intraperitoneal administration of graded doses of the test compound Other modes of administration may also be used. The animals' survival time in a temperature controlled hypoxic environment (96% nitrogen and 4% oxygen) is recorded. A statistical comparison is made between coincident vehicle-treated animals and the experimental group. The dose-response and minimum active dose (MAD) for compounds are obtained.

The following non-limiting illustrations and examples are provided to exemplify the preparation of the intermediate amines of formula (2) and their conversion to the novel compounds of general formula (1).

PREPARATION OF INTERMEDIATES

Illustration 1

Preparation of 1,2-Diphenyl-2-propylamine hydrochloride.

This compound was prepared by suitable modification of the procedures described by Christol, *Bull. Soc. Chim. Fr.*, 1963, 4, 877, and Ho and Smith, Tetrahedron, 1970, 26, 4277 as follows. To a suspension of sodium cyanide (34.3 g, 0.7 mol) in 500 ml of glacial acetic acid and 100 ml of n-butylether at 0° C. was added portionwise 200 ml of concentrated sulfuric acid. The ice bath was removed and a solution of 1,2-diphenyl-2-propanol (106 g, 0.5 ml) in 100 ml of n-butylether was added dropwise over a period of 2 hours, then the mixture stirred for 48 hours. The mixture was poured into 1000 cc of ice, and extracted with chloroform. The extracts were washed with water, dried and evaporated to a solid residue which was stirred with hexane (500 ml), filtered and dried to give 85.35 g (72% yield) of N-formyl-1,2-diphenyl-2-propylamine, mp 97°-99° C. This was suspended in 1 L of 10% HCl and heated to reflux for 2.5 hours. After cooling in air for 1 hour then in an ice bath for 30 minutes, the white solid which had crystallized was collected by filtration and vacuum dried to give 85.9 g (97% yield) of 1,2-diphenyl-2-propylamine hydrochloride, mp 175°-178° C.

Illustration 2

Preparation of N-Methyl-1,2-diphenylethylamine.

To a stirred two phase solution of 1,2-diphenylethylamine (30.0 g, 0.15 mol) in 300 ml of methylene chloride and 500 ml of water was added sodium carbonate (23.9 g, 0.225 mol) and the solution was cooled to 10° C. under nitrogen. Ethyl chloroformate (21.5 ml, 0.225 mol) was added dropwise over a 1 hour period. The reaction was warmed to ambient temperature and stirred at that temperature for 3 hours. The phases were separated and the aqueous phase was extracted with methylene chloride (75 ml). The combined methylene chloride extracts were washed with 1N HCl (200 ml), dried and evaporated to a white solid, 40.3 g. Recrystallization from cyclohexane gave N-carboethoxy-1,2-diphenylethylamine, mp 74°-75° C.

To a stirred suspension of lithium aluminum hydride (12.4 g, 0.32 mol) in 300 ml of tetrahydrofuran at 0° C. under nitrogen was added dropwise a solution of N-carboethoxy-1,2-diphenylethylamine (35.0 g, 0.13 mol) in 200 ml of tetrahydrofuran. The mixture was heated to reflux for 8 hours. The mixture was cooled in an ice-water bath and water (13 ml), 15% NaOH (13 ml) and water (39 ml) were carefully added to the mixture. The mixture was warmed to ambient temperature and the precipitated salts were removed by filtration through celite. Removal of solvent gave N-methyl-1,2-diphenylethylamine, 26.8 g as a colorless oil.

Treatment of this oil with maleic acid in ethyl acetate and methanol gave N-methyl-1,2-diphenylethylamine maleate, mp 129°-31° C.

Illustration 3

Preparation of N-Methyl-1.2-diphenyl-2-propylamine hydrochloride.

N-formyl-1,2-diphenyl-2-propylamine (23.6 g, 0.1 mol) was added to a stirred suspension of LiAlH$_4$ (15.0 g, 0.395 mol) in 1 L of dry tetrahydrofuran. After 2 hours the mixture was heated at 35° C. for 22 hours, then refluxed for 2 hours, and allowed to cool to room temperature. Water was added to decompose the excess LiAlH$_4$, and the mixture filtered to remove solid salts. Evaporation of the solvent gave 23.0 g of the crude product as a yellow oil. This was dissolved in 180 ml of ethyl acetate and 20 ml of isopropanol and acidified with HCl gas. Upon standing a white sold crystallized which was collected by filtration and vacuum dried at 65° C. to give 21.7 g (84%) of N-methyl-1,2-diphenyl-2-propylamine hydrochloride; mp 200°-201° C.

Illustration 4

Preparation of (−)-1,2-Diphenyl-2-propylamine.

Racemic 1,2-diphenyl-2-propylamine (86 g, 0.4 mol) was dissolved in 0.5 L 95% ethanol, heated to near reflux and added to a solution of (−)-dibenzoyltartaric acid monohydrate (151.9 g, 0.4 mol) in 0.5 L 95% ethanol also at reflux. A white solid crystallized immediately. The mixture was refluxed for 5 minutes, then allowed to cool to ambient temperature. The solid was collected by filtration and dried to give 86.2 g [α]$_D$=94.2°, C=0.5, CH$_3$OH). The filtrate was saved. The solid was suspended in 0.9 L of 95% ethanol, stirred and heated to reflux for 1 hour, allowed to cool to ambient temperature and the white solid collected by filtration and vacuum dried at 80° C. for 8 hours to give 60.2 g of (−)-1,2-diphenyl-2-propylamine-(−)dibenzoyl tartrate, mp 194°-195° C.; [α]$_D$=−96.0° (C=0.5, CH$_3$OH). 5.0 g of this salt was dissolved in 250 ml CHCl$_3$ and 200 ml 5% NH OH shaken vigorously, the layers separated and the organic phase washed with 3×200 ml 5% NH$_4$OH, 2×200 ml H$_2$O and dried over MgSO$_4$. The solvent was evaporated to give 1.75 g of (−)-1,2-diphenyl-2-propylamine as an oil. The maleate salt was prepared by dissolving this oil in 25 ml of ethylacetate and adding the solution to a hot solution of maleic acid (1.02 g, 8.87 mmol) in 50 ml of 3/1 ethylacetate/isopropanol. Upon cooling a white solid crystallized, which was collected by filtration and vacuum dried to give 2.05 g of (−)-1,2-diphenyl-2-propylamine maleate, mp 176°-177° C., [α]$_D$=27.4°, (C=1, CH$_3$OH).

Illustration 5

Preparation of (+)-1,2-Diphenyl-2-propylamine.

The filtrate residue which was saved in Illustration 4, was treated with 1 L CHCl$_3$ and 0.9 L 5% NH$_4$OH, shaken vigorously, the layers separated and the organic phase washed with 4×800 ml 5% NH$_4$OH and 2×500 ml H$_2$O, then dried over MgSO$_4$ and evaporated to an oil 32.3 g, which is enriched in (+)-1,2-diphenyl-2-propylamine. This oil (32. 3 g, 0.153 mol) was dissolved in 200 ml hot 95% ethanol and added to a stirred solution of (+)-dibenzoyl tartaric acid monohydrate (57.55 g, 0.153 mol) in 600 ml of refluxing 95% ethanol. A white solid crystallized immediately, which was stirred at reflux for 5 minutes, then allowed to cool to ambient temperature. The solid was collected by filtration and vacuum dried at 80° C. for 8 hours to give 71.6 g of (+)-1,2-diphenyl-2-propylamine (+)-dibenzoyltartrate, mp 197°-198° C., [α]$_D$=+95.8°, (C=0.5, CH$_3$OH). 5.0 g of this salt was dissolved in 250 ml CHCl$_3$ and 200 ml 5% NH$_4$OH, shaken vigorously, the layers separated and the organic phase washed with 3×200 ml 5% NH$_4$OH and 2×200 ml H$_2$O dried over MgSO$_4$. The solvent was evaporated to give 1.75 g of (+)-1,2-diphenyl-2-propylamine as an oil. The maleate salt was prepared by dissolving this oil in 25 ml ethyl acetate and adding the solution to a hot solution of maleic acid (1.02 g, 8.78 mmol) in 50 ml 3/1 ethyl/acetate/isopropanol. Upon cooling a white solid crystallized, which was collected by filtration and vacuum dried to give 2.06 g of (+)-1,2-diphenyl-2-propylamine maleate, mp 177°-178° C., [α]$_D$=+27.3° (C=1, CH$_3$OH).

EXAMPLE 1

Preparation of
N-(1,2-diphenyl-1-methylethyl)-2S-pyrrolidinecarboxamide

To a stirred solution of 1,2-diphenyl-2-propylamine (0.085 mol) in 500 ml of chloroform under nitrogen was added N-CBZ-L-proline (0.11 mol), and then a solution of dicyclohexylcarbodiimide (0.1 mol) in 100 ml of chloroform and the mixture stirred for 14 hours. The precipitated solid was removed by filtration and the solvent evaporated. The residue was dissolved in 500 ml of methylene chloride, filtered and evaporated to a yellow oil. This was treated with ether (750 ml) and 500 ml of ice cold water, basified with 5 ml of 50% NaOH, the layers shaken and separated. The ether layer was washed with water (2×125 ml), dried and evaporated to an oil. This was dissolved in 500 ml of methanol and 50 ml of 10% HCl, and hydrogenated at 40 psi in a Parr apparatus over 3.0 g of 10% Pd/C catalyst for 4 hours. The catalyst was removed by filtration, and the solvent evaporated to a white solid. This was dissolved in 80 ml of hot methanol and treated with 200 ml of ether. Upon cooling a solid crystallized which was recrystallized from 100 ml of isopropanol and 100 ml of methanol to give of N-(1,2-diphenyl-1-methylethyl)-2S-pyrrolidinecarboxamide hydrochloride, which after vacuum drying at 80° C. for 24 hours had mp 99–102° C.

EXAMPLE 2

Preparation of
N-(1,2-diphenyl-1-methylethyl)-2R-pyrrolidinecarboxamide

By procedures essentially the same as those described in Example 1 and by substituting N-CBZ-D-proline for N-CBZ-L-proline; the corresponding N-(1,2-diphenyl-1-methylethyl)-2R-pyrrolidinecarboxamide, mp 91°–95° C., is prepared.

EXAMPLE 3

Preparation of
N-(1,2-diphenyl-1-methylethyl)-2-piperidinecarboxamide hydrochloride By procedures essentially the same as those described in Example 1 and by substituting N-CBZ-pipecolinic acid for N-CBZ-L-proline; the corresponding N-(1,2-diphenyl-1-methylethyl)-2-piperidinecarboxamide hydrochloride, mp 233°–237° C., is prepared.

EXAMPLE 4

Preparation of
N-(1,2-diphenyl-1-methylethyl)-L-thiazolidine-4-carboxamide hydrochloride To a stirred solution of 1,2-diphenyl-2-propylamine (14.94 g, 0.071 mol) and BOC-L-thiazolidine-4-carboxylic acid (6.5 g, 0.071 mol) in 350 ml of chloroform was added dicyclohexylcarbodiimide (14.61 g, 0.071 mol) and the mixture stirred for 16 hours, filtered and evaporated to an oily residue. This was dissolved in ethylacetate (200 ml), filtered and an additional 200 ml of ethylacetate added. The solution was washed with 5% cold HCl (2×200 ml), dried and evaporated to a pale yellow oil, 26.4 g. This was dissolved in 200 ml ethylacetate and acidified with HCl gas. Upon standing a solid was obtained which was recrystallized from 200 ml of ethanol and then 200 ml of 1:1 isopropanol:ethanol containing a trace of water to give after drying N-(1,2-diphenyl-1-methylethyl)-L-thiazolidine-4-carboxamide hydrochloride as a white solid, mp 229°–230° C.

EXAMPLE 5

Preparation of
N-(1,2-Diphenylethyl)-2S-pyrrolidine-carboxamide

By procedures essentially the same as those described in Example 1 and by substituting 1,2-diphenylethylamine for 1,2-diphenyl-2-propylamine; the corresponding N-(1,2-diphenylethyl)-2S-pyrrolidinecarboxamide may be prepared.

EXAMPLE 6

Preparation of
N-Methyl-N-(1,2-Diphenylethyl)-2S-pyrrolidinecarboxamide

By procedures essentially the same as those described in Example 1 and by substituting N-methyl-1,2-diphenylethylamine for 1,2-diphenyl-2-propylamine; the corresponding N-methyl-(1,2-diphenylethyl)-2S-pyrrolidine-carboxamide may be prepared.

EXAMPLE 7

Preparation of
N-Methyl-N-(1,2-diphenyl-1-methylethyl)-2S-pyrrolidinecarboxamide By procedures essentially the same as those described in Example 1 and by substituting N-methyl-1,2-diphenyl-2-propylamine for 1,2-diphenyl-2-propylamine; the corresponding N-methyl-N-(1,2-diphenyl-1-methylethyl)-2S-pyrrolidinecarboxamide may be prepared.

EXAMPLE 8

Preparation of
N-(1R-1,2-Diphenyl-1-methylethyl)-2S-pyrrolidinecarboxamide and
N-(1S-1,2-diphenyl-1-methylethyl)-2S-pyrrolidinecarboxamide By procedures essentially the same as those described in Example 1 and by substituting (+)-1,2-diphenyl-2-propylamine or (−)1,2-diphenyl-2-propylamine for (+/−)-1,2-diphenyl-2-propylamine, either the corresponding N-(1R-1,2-diphenyl-1-methylethyl)-2S-pyrrolidinecarboxamide or N-(1S-1,2-diphenyl-1-methylethyl)-2S-pyrrolidinecarboxamide may be prepared essentially free of enantiomeric and diastereoisomeric forms.

What is claimed:

1. A compound of the formula

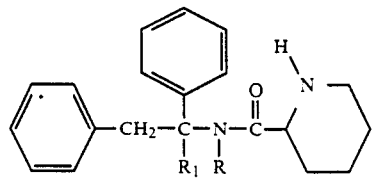

wherein R and $R_1$ are independently selected from hydrogen and methyl.

2. N-(1,2-diphenyl-1-methylethyl)-2-piperidinecarboxamide hydrochloride.

* * * * *